United States Patent [19]

Wardlaw

[11] Patent Number: 4,558,947
[45] Date of Patent: Dec. 17, 1985

[54] METHOD AND APPARATUS FOR MEASURING BLOOD CONSTITUENT COUNTS

[76] Inventor: Stephen C. Wardlaw, 128 Sunset Hill Dr., Branford, Conn. 06405

[21] Appl. No.: 549,319

[22] Filed: Nov. 7, 1983

[51] Int. Cl.⁴ .................. G01N 33/48; G01N 21/90; G01N 15/02; G01N 21/00
[52] U.S. Cl. ........................................ 356/39; 73/57; 356/40; 356/336; 356/338; 356/427
[58] Field of Search ............... 73/57; 356/39, 40, 336, 356/338, 427

[56] References Cited
U.S. PATENT DOCUMENTS 4,156,570  5/1978  Wardlaw ......................... 356/36
4,350,441  9/1982  Wicnienski ........................ 356/40

Primary Examiner—Michael R. Lusignan
Attorney, Agent, or Firm—William W. Jones

[57] ABSTRACT

Blood constituents such as red cells, white cells, and platelets are centrifuged into layers in a capillary tube and the true extent of one or more of the layers is measured photometrically. Each layer to be measured is optically scanned by a sequence of scanning operations with the actual extent of each layer traverse being recorded in a computer. After each layer has been completely circumferentially scanned and each traverse recorded, the computer determines the true average axial dimension for each layer and computes, through prior input, the actual constituent count for each constituent layer.

23 Claims, 9 Drawing Figures

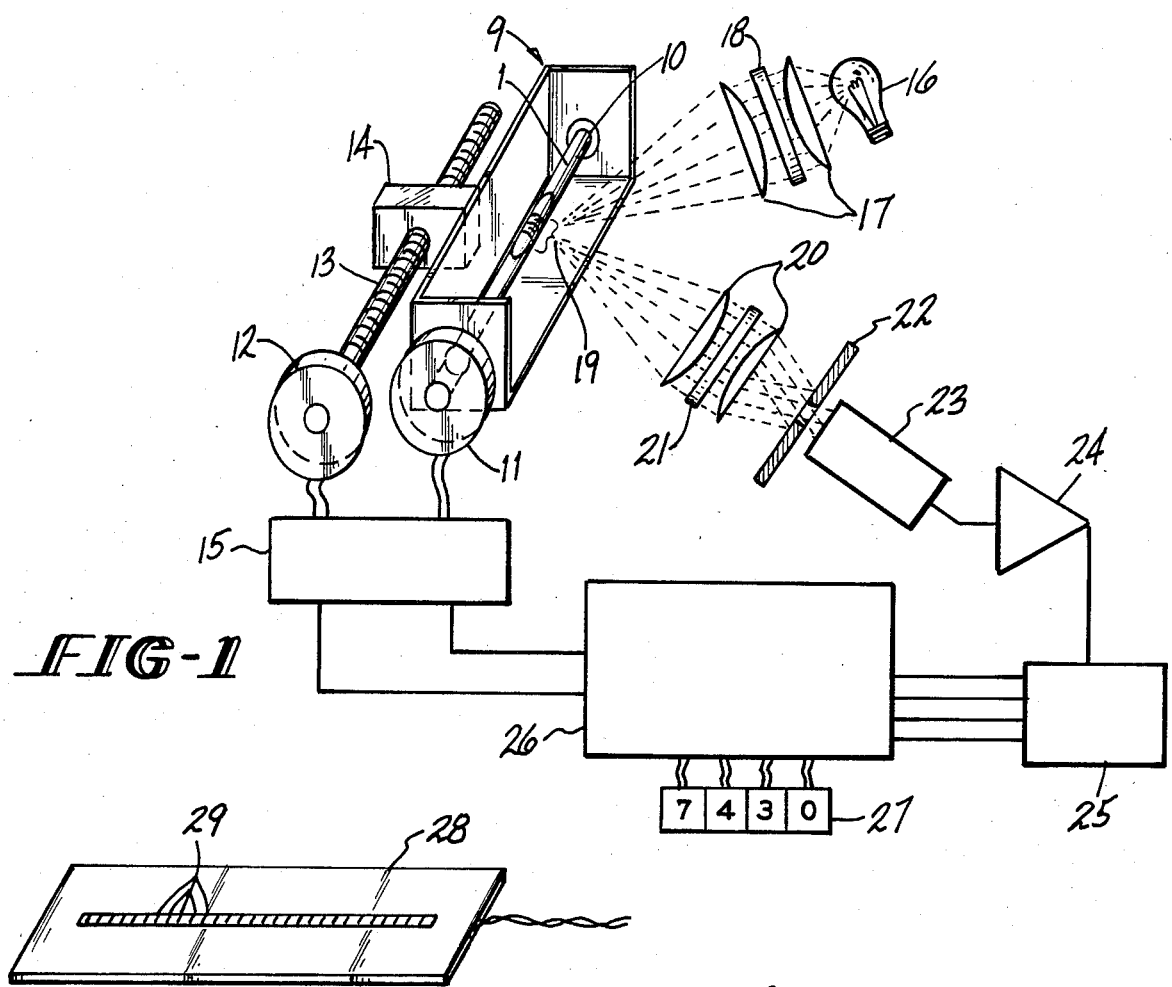
FIG-1
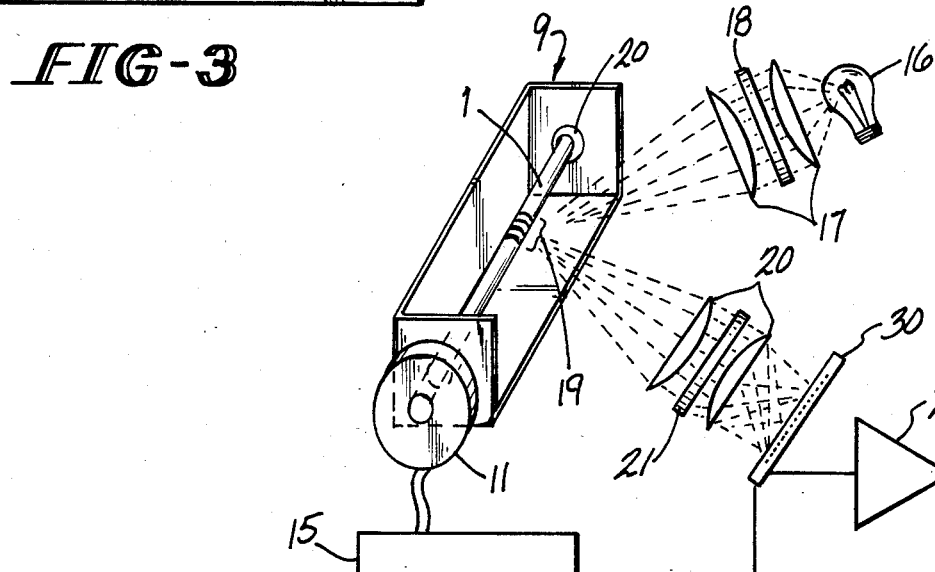
FIG-3
FIG-2

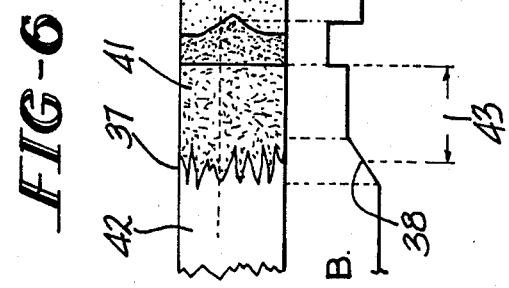
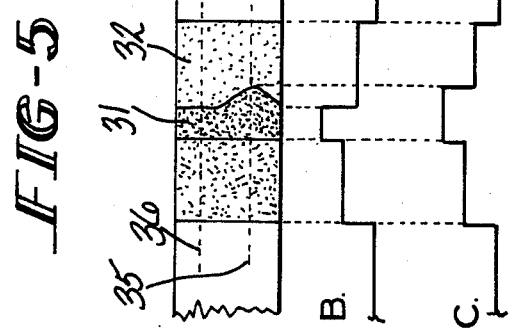
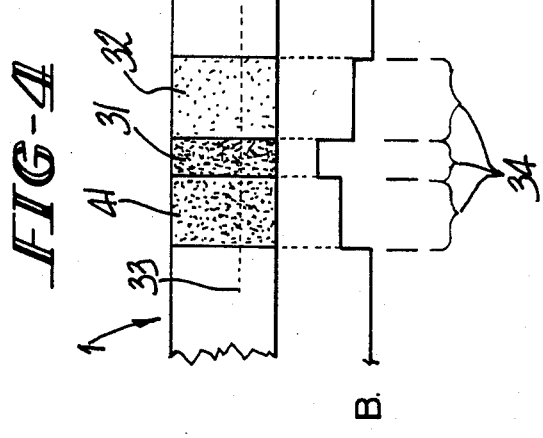
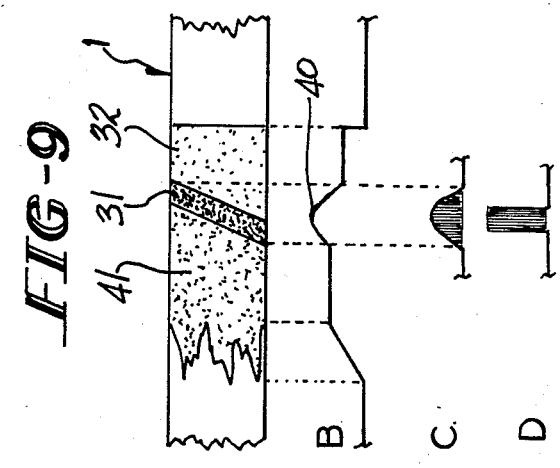
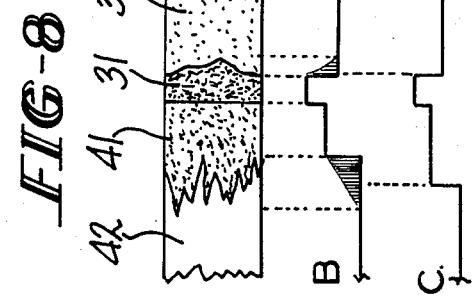
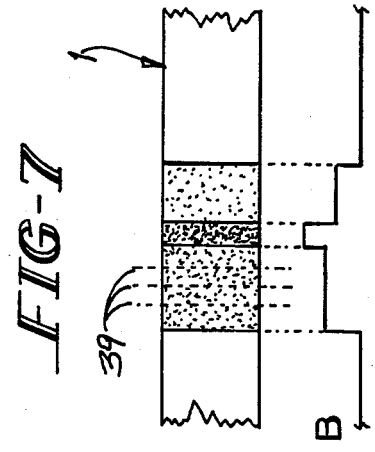

METHOD AND APPARATUS FOR MEASURING BLOOD CONSTITUENT COUNTS

This invention relates to an improved method and apparatus for measuring substantially accurate blood constituent counts in a centrifuged sample of anticoagulated whole blood.

U.S. Pat. Nos. 4,027,660; 4,082,085; and 4,137,755 relate to apparatus and methodology for physically elongating blood constituent layers in a centrifuged capillary tube blood sample. U.S. Pat. No. 4,156,570 relates to an instrument for obtaining blood constituent counts from the physically elongated constituent layers derived as in the first referenced patents.

Generally speaking, the above-referenced patents describe a procedure wherein an anticoagulated whole blood sample is disposed in a capillary tube along with an elongated float body. The float body is generally cylindrical in configuration and is provided with an outside diameter which is a predetermined amount smaller than the bore diameter of the capillary tube. This forms an annular free space or void in the tube between the outside surface of the float body and the bore of the tube. The contained sample and float body are centrifuged so as to cause the blood constituents to layer out in the tube bore thereby forming a red cell layer; a buffy coat layer comprising granulocytes, lymphocytes/monocytes, and platelets; and a plasma layer. The specific gravity of the float body is such that it floats in the red cell layer and extends through the buffy coat layer into the plasma. This causes the buffy coat constituents to be crowded into the annular free space thereby resulting in physical elongation of the several buffy coat constituent layers. A stain is preliminarily added to the blood sample which differentially colors the various blood component layers so that the latter appear as differentially colored bands in the capillary tube after centrifugation. The capillary tube is then positioned in the instrument which forms the subject of U.S. Pat. No. 4,156,570 where it is spun about its longitudinal axis and is exposed to a source of light which causes the stain to fluoresce. Each layer fluoresces a different color, and any unevenness of the various layer interfaces will disappear due to the spinning of the tube. The axial extent of each layer is then measured as the tube spins, and the measurements are converted into constituent counts. In this manner, approximate constituent counts can be obtained for medical screening purposes.

The above methodology is quite acceptable in the majority of cases because there occurs relatively even interfaces between the layers in most cases. It has been noted, however, that constituent count discrepancies can occur and will occur when the interfaces between adjacent layers are unusually irregular in formation. Such irregularity can occur when the tube is roughly handled or when the ambient temperature is too high. Since the radial thickness of each layer is fixed, and since the circumferential dimension of the tube bore is fixed, the volume of cells in each layer is proportioned to the axial extent of each layer. The difficulty encountered when the cell layer interfaces are noticeably irregular is overcome in accordance with this invention by direct measurement of the true axial dimension of the layers. The true axial dimension is obtained by taking a sequence of individual axial dimension measurements about the circumference of the tube (and thus the layers), and then averaging the individual measurements to find the true axial dimension of each layer. The cell counts of each layer can then be determined once the true axial dimension is known. This invention provides an automated procedure and apparatus for directly measuring the layers to find their true axial dimension.

It is, therefore, an object of this invention to provide a method and apparatus for determining cell counts in centrifuged layers of component cells in a centrifuged capillary tube sample of anticoagulated whole blood wherein the layers may be bounded by irregular interfaces.

It is a further object of this invention to provide a method and apparatus of the character described wherein direct measurement of the true axial dimension of one or more cell layers is made.

It is yet another object of this invention to provide a method and apparatus of the character described wherein the true axial dimension of the cell layer or layers is determined by averaging a series of sequential actual axial measurements made by repeated optical scanning of a rotated capillary tube.

These and other objects and advantages of this invention will be more readily apparent from the following detailed description of preferred embodiments of the method and apparatus thereof when taken in conjunction with the accompanying drawings, in which:

FIG. 1 is a somewhat schematic perspective view of a preferred embodiment of an apparatus for performing cell count measurements in accordance with this invention;

FIG. 2 is a somewhat schematic perspective view of a second embodiment of an apparatus for performing cell count measurements in accordance with this invention;

FIG. 3 is a perspective view of a component of the apparatus of FIG. 2;

FIG. 4 is a schematic plan view of a first cell layer interface which may be achieved by centrifugation;

FIG. 5 is a schematic plan view of a second cell layer interface which may be achieved by centrifugation;

FIG. 6 is a schematic plan view of a third cell layer interface which may be achieved by centrifugation;

FIG. 7 is a schematic plan view of a cell layer interface similar to that shown in FIG. 4;

FIG. 8 is a schematic plan view of a cell layer interface similar to that shown in FIG. 6; and FIG. 9 is a schematic plan view of a fourth cell layer interface which may be achieved by centrifugation.

Referring now to the drawings, there is shown in FIG. 1 a schematic perspective view of one preferred embodiment of an apparatus formed in accordance with this invention. It will be understood that the blood sample-containing tube 1 shown in the drawing contains a centrifuged anticoagulated whole blood sample and a float body as described in the aforesaid U.S. Pat. No. 4,082,085. The tube 1 is supported at each end by self-centering spring loaded mandrels 10 which are incrementally rotated by a stepping motor 11. The motor 11 preferably rotates the mandrels 10 and tube 1 through successive angles of about 6° or 360° as will be explained hereinafter. The mandrels 10 and motor 11 are mounted on a frame 9 which, in turn, is secured to an internally threaded bushing block 14. The block 14 receives a threaded rod 13, which is rotated by a reversible stepping motor 12. The motor 12 and the rod 13 are mounted on a fixed frame (not shown) and the block 14 is keyed to the fixed frame so that the block 14, frame 9, motor 11, mandrels 10 and tube 1 will undergo reciprocal linear movement in the direction of the axis of the tube 1 as the rod 13 is rotated by the motor 12. Thus, as the motor 12 operates through a forward and reverse cycle, the rod 1 will move in one direction along its axis and return in the opposite direction. The extent of movement is such that the buffy coat-containing area 19 of the tube 1 can be scanned by the apparatus in the manner detailed hereinafter. The stepping motors 11 and 12 are driven by a stepping motor driver 15.

A light source, such as a quartz-halogen lamp 16, is mounted on the fixed frame so as to direct light toward the area 19 of the tube 1. Lenses 17 are operable to focus light emitted by the lamp 16 on the area 19 of the tube. A suitable filter 18 is disposed so as to block all wavelengths of light from the lamp 16 except those required to excite fluorescence of the dye in the blood sample. When acridine orange is used as the dye in the blood sample, the excitation wavelength is centered near 460 nm, and the wavelengths of the light emitted by the fluorescing dye are centered near 560 nm and 680 nm.

The emitted light is collected by lenses 20 and passes through a filter 21 which blocks passage of all wavelengths of light except the emitted light wavelengths. In particular, the filter 21 should operate to block passage of the exciting wavelengths of light from the lamp 16. A phototube 23 measures the intensity of the light waves passing through the lenses 20 and filter 21. A diaphragm 22 is positioned in front of the phototube 23 so as to restrict the field of light passing to the phototube 23 to a spot which, in this instance, is preferably about 100 microns in diameter. An amplifier 24 is connected to the phototube 23 and is operable to amplify the photoelectric signals generated by the phototube 24 and transmit the amplified signals to a converter 25, which converts the signals from analog to digital form. The converter 25 is connected to a computer 26. The computer 26 controls the converter 25 and also controls the stepping motors 11 and 12. The computer 26 can operate the device in one of two ways. The computer 26 can direct the converter 25 to take a reading and at the same time direct the stepping motor 11 to rotate the tube 1 stepwise through a 360° angle. The readings are then stored in the computer 26. The computer then directs the stepping motor 12 to rotate the rod 13 through a known angle which will move the tube 1 a distance of 100 microns (the size of the window in the diaphragm 22). After the tube 1 is thus axially shifted, the computer 26 directs the converter 25 to take another set of readings and while directing the stepping motor 11 to once again rotate the tube 1 stepwise through another 360° angle. The second readings are then stored in the computer 26 and the procedure repeated a third time. The procedure is repeated until the entire target area 19 of the sample has been scanned and read. An alternative mode of operation involves the computer 26 directing the converter 25 to take a reading and then directing the stepping motor 12 to incrementally rotate the rod 13 sufficiently to shift the tube 1 axially so as to cause the entire axial extent of the target area 19 to be scanned. The readings are stored in the computer 26, and the computer 26 then directs the stepping motor 11 to rotate the tube 1 through a substantially 6° angle. The converter 25 is then directed to take another set of readings while the stepping motor 12 is directed to incrementally rotate the rod 13 in the opposite direction so as to shift the tube 1 back through the entire extent of the target area 19. This second procedure can then be repeated until the entire circumference of the target area 19 has been read and stored. In either of the above modes, the intensity of fluorescence of the entire target area 19 of the sample is mapped in the computer memory. The extent or area of each of the cell bands is then calculated by the computer 26 and converted into cell counts by use of cell size information, and radial band thickness information (the latter of which is equal to the radial thickness of the void or free space between the float body and the tube bore), which information has been previously inputted into the computer 26. The actual cell counts are then sequentially displayed in the digital readout frames 27.

Referring now to FIG. 2, there is shown an alternative form of a reader apparatus which may be used. In the apparatus of FIG. 2, certain components are the same as in FIG. 1, and like numerals are used to designate such components. The apparatus of FIG. 2 includes mandrels 10 for holding the ends of the tube 1, which mandrels 10 are mounted in a frame 9 and rotated by a stepping motor 11 controlled by stepping motor driver 15. A lamp 16 is focused on target area 19 of the sample in the tube 1 by lenses 17, and the light emitted by the lamp 16 is filtered by filter 18, as previously described. Light emitted by the sample is focused by lenses 20 through a selective filter 21 onto a linear array of photocells denoted generally by the numeral 30. The array 30, as seen in FIG. 3, includes a flat insulating substrate 28 on which there is placed a linear array of photocells 29. There can be as many as 1,024 photocells in a single commercially available array of the type shown in FIG. 3. The photosensing elements may be either of the diode (Reticon) or charge-coupled (Fairchild) type. When the image of the target area 19 is focused by the lenses 20 onto the photocells 29 in the array 30 through the filter 21, fluorescence intensity readings from each single cell 29 in the array 30 can be amplified by the amplifier 24 and converted into a digital signal by the converter 25 and fed into the computer 26, as previously described. Since the intensity of fluorescence of a linear segment of the entire target area 19 is measured at once, the need to move the tube 1 axially is eliminated, and the tube 1 need only be rotated about its axis to bring the next circumferential region into view. Thus, the embodiment of FIG. 2 is less complex mechanically than the embodiment of FIG. 1. On the other hand, the arrays used in the embodiment of FIG. 2 may be somewhat less sensitive to light than the phototube used in the embodiment of FIG. 1 and, thus, may not be as accurate in some instances.

Referring to FIGS. 4-9, there are shown various cell interfaces which may be formed by centrifugation of the blood sample along with schematic representations of the "map" of the cell layers which the computer has inputted into it from the converter. In FIG. 4, it will be noted that the granulocyte band 41, the lymphocyte/monocyte band 31 and the platelet band 32 have clear, sharp interfaces in the centrifuged sample. Examination of pixels along line 33 by the computer will produce a histogram B shown in FIG. 4. The horizontal axis of the histogram represents distances along the longitudinal axis of the blood sample, and the vertical axes in the histogram represent the various fluorescent intensities of the various cells. With a sample as shown in FIG. 4, the computer need only search for obvious discontinuities in fluorescence and measure the distances 34 between such discontinuities. Once the distances 34 are measured by the computer, they are multiplied by the known calibration factors to derive the various cell counts.

FIG. 5 shows a sample wherein the interface between the layers 31 and 32 is distorted by a bulge. The two histograms B and C in FIG. 5 show that single readings taken along line 35 and 36 would indicate different axial dimensions for the cell layer 31 if such measurements were only made along lines 35 and 36. The computer obviates this problem, however, by averaging all of the separate measurements taken as the successive longitudinal scans are performed.

FIG. 6 shows a similar problem which arises with a jagged interface 37 between the cell layers 42 and 41. The histogram B for the sample in FIG. 6 will have a sloping interface 38 whereby the geometric mean of that sloping line 38 will provide the correct line to begin measurement of the axial dimension 43 of the cell layer 41. This geometric mean is calculated, as before, by the computer by analyzing each successive scan.

FIG. 7 shows a well delineated sample similar to FIG. 4 and shows the histogram B which is produced by circumferential sequential scans taken along lines 39. As with FIG. 4, the histogram will have well defined abrupt discontinuities which will be noted by the computer with no averaging being necessary.

FIG. 8 shows a sample which is similar to that shown in FIG. 6 in that the interface between the layers 41 and 42 is indistinct and the interface between the layers 31 and 32 is irregular. The histogram B of the sample in FIG. 8 shows the average circumferential readings, i.e., the readings taken in the direction of lines 39 shown in FIG. 7. The shaded areas of the histogram B represent the areas which must be interpolated to derive the corrected layer extents. This is performed by the computer by calculating the area of each shaded portion and converting it to a band length increment, assuming the same color intensity as the full intensity readings, which are delineated by the horizontal lines on the histogram B in FIG. 8. The corrected histogram is shown at C in FIG. 8.

FIG. 9 shows a layer formation in the cell layer 31 which can present a complicated problem when the scans are taken in the circumferential direction, as along the lines 39 shown in FIG. 7. In this type of layering, each linear scan can include some of the surrounding layers 41 or 32. This condition results in a histogram as shown at B in FIG. 9. In the area marked 40 in the histogram, there is no definable plateau of intensity, thus any interpretation of the width of the area 40 at this point would be erroneous. When such a condition is noted by the computer, it is programmed to perform a Fourier transformation of the irregular curve 40 with the result being shown at C in FIG. 9. The shaded area under the curve C of FIG. 9 represents the area of the layer 31. If the maximum intensity of the layer 31 is known, then the computer can calculate the true axial dimension of the layer 3 as shown at D in FIG. 9. To obtain the maximum intensity, it is only necessary to stop rotation of the tube and take one longitudinal or axial scan, locating and measuring the peak intensity of the layer in question.

These techniques could also be applied to the analysis of other regions of the blood sample. The reticulocytes (newly formed red blood cells) lie in a diffuse band adjacent to the granulocytes. The effective axial dimension of the reticulocyte layer can be calculated in a similar manner. The stains used to differentiate the cell layers do not have to be fluorescent. The apparatus can be adapted to detect reflected light from the tube if the first filter 18 is removed, thereby determining absorption of light. If the diaphragm window were made small enough, about 20 microns in diameter, physical expansion of the buffy coat would not be required.

Since many changes and variations of the disclosed embodiments of the invention may be made without departing from the inventive concept, it is not intended to limit the invention otherwise than as required by the appended claims.

What is claimed is:

1. An optical scanning apparatus for measuring blood cell counts in a centrifuged sample of anticoagulated whole blood contained in a transparent tube wherein the blood cell types are separated into different layers in the tube, said apparatus comprising:
   (a) means for supporting the tube;
   (b) a source of light operable to illuminate the blood cell layers in the tube;
   (c) photosensor means focused on the illuminated blood cell layers in the tube and operable to scan the cell layers to detect differing light intensities characteristic of the different cell types in the layers of cells;
   (d) means for causing relative movement between the tube and said photosensor means for enabling said photosensor means to scan the layers of blood cells at all different locations circumferentially of the tube;
   (e) converter means operably connected to said photosensor means for converting analog signals from said photosensor means to digital form; and
   (f) computer means operably connected to said converter means for receiving and storing digital signals from said converter means, said computer means further being operable to utilize the signals received to calculate the average axial dimension of each layer of cells scanned to determine from previously inputted data the true cell counts for each layer of cells scanned.

2. The apparatus of claim 1 further comprising a diaphragm interposed between said photosensor means and the tube, said diaphragm having a window operable to limit the field of view of the tube available to said photosensor means.

3. The apparatus of claim 2 wherein said window has a diameter of approximately 100 microns.

4. The apparatus of claim 2 wherein said window has a diameter of approximately 20 microns.

5. The apparatus of claim 1 further comprising first filter means disposed between said source of light and the tube, said first filter means being operable to limit the wavelengths of light transmitted to the tube from said source of light.

6. The apparatus of claim 5 further comprising second filter means disposed between said photosensor means and the tube, said second filter means being operable to limit the wavelengths of light transmitted to said photosensor means from the cell layers.

7. The apparatus of claim 1 wherein said means for causing relative movement comprises a stepping motor for rotating the tube about its axis and which is operably connected to and controlled by said computer means.

8. The apparatus of claim 7 wherein said stepping motor is operable to rotate the tube through sequential 360° angles.

9. The apparatus of claim 7 wherein said stepping motor is operable to rotate the tube through sequential angles approximately equal to 6°.

10. The apparatus of claim 1 wherein said photosensor means comprises a linear array of photocells operable to scan the entire axial extent of cell layers being measured.

11. The apparatus of claim 10 wherein said means for causing relative movement is operable to rotate the tube stepwise about its axis through sequential incremental angles of about 6°.

12. The apparatus of claim 1 further comprising means for moving the tube axially a distance at least equal to the composite axial dimension of all of the cell layers being scanned.

13. The apparatus of claim 12, wherein said means for moving the tube axially comprises a second stepping motor operably connected to and controlled by said computer means, said second stepping motor being operable to rotate a threaded rod about its axis with said threaded rod being threadably connected to a keyed bushing secured to a movable frame on which said means for rotating the tube, said means for supporting the tube, and said second stepping motor are mounted.

14. The apparatus of claim 1, further comprising amplifier means interposed between said photosensor means and said converter means to amplify the analog signals transmitted from said photosensor means prior to conversion thereof to digital signals.

15. A method for measuring blood cell counts in a centrifuged sample of anticoagulated whole blood contained in a transparent tube wherein the blood cell types are separated into different layers in the tube, said method comprising the steps of:
(a) illuminating the cell layers to be measured with a light which produces differing light intensity characteristics in the different cell types being measured;
(b) scanning the entire outer circumferential surface of each cell layer being measured with a photosensor which detects differing light intensity characteristics produced by illumination of the different cell types being measured and which photosensor produces an analog output which varies in proportion to the different intensities of light detected in the cell layers;
(c) converting said analog output to digital output;
(d) receiving and storing said digital output in a computer and thereafter computer analyzing said stored digital output to compute an average axial dimension for each layer of cells scanned and determining in said computer the true cell counts for each layer of cells scanned from the computed average axial dimension and additional previously inputted data stored in said computer.

16. The method of claim 15 comprising the step of moving the tube so as to pass the entire outer circumferential surface of each cell layer being measured through a focal point of said photosensor.

17. The method of claim 16 wherein said step of moving the tube includes rotating the tube about its axis.

18. The method of claim 17 wherein the tube is rotated about its axis in sequential incremental angles of about 6°.

19. The method of claim 17 wherein the step of moving the tube further includes imparting reciprocal axial movement to the tube so that the full axial extent of each layer of cells being scanned is passed through said focal point of said photosensor.

20. The method of claim 19 wherein all movement of the tube is controlled by said computer.

21. The method of claim 15 wherein the blood cells are stained and wherein said light illuminating the cell layers is restricted to wave lengths which excite the stained cells to fluoresce at different characteristic intensities.

22. The method of claim 15 wherein said scanning step is performed with a linear array of photocells.

23. A method for measuring blood cell counts in a centrifugal sample of anticoagulated whole blood contained in a transparent tube wherein the blood cell types are separated into different layers in the tube, said method comprising the steps of:
(a) providing a light source;
(b) focusing light emitted from said light source on an area corresponding to the outside surface of the tube portion containing the cell layers being measured;
(c) scanning the entire outer circumferential surface of each cell layer being measured with a photosensor which detects differing light intensity characteristics produced by illumination of the different cell types being measured and which photosensor produces an analog output which varies in proportion to the different intensities of light detected in the cell layers;
(d) providing a computer having stored in its memory data concerning the available volume in the tube in which the cell layers being measured reside and data concerning the respective sizes of the various cell types being measured;
(e) converting said analog output to digital output;
(f) receiving and storing said digital output in said computer and thereafter computer analyzing said stored digital output to compute an average axial dimension for each layer of cells scanned and determining in said computer the true cell counts for each layer of cells scanned from combining the computed average axial dimension with the available volume memory data and the respective cell size memory data; and
(g) providing a visual indication of computed true cell counts.

* * * * *